United States Patent
Akashika et al.

(10) Patent No.: US 10,731,226 B2
(45) Date of Patent: Aug. 4, 2020

(54) METHOD FOR QUANTIFYING ADENO-ASSOCIATED VIRUS

(71) Applicant: TAKARA BIO INC., Kusatsu-shi, Shiga (JP)

(72) Inventors: Tamaki Akashika, Kusatsu (JP); Katsuyuki Dodo, Kusatsu (JP); Masanari Kitagawa, Yasu (JP)

(73) Assignee: TAKARA BIO INC., Kusatsu-Shi (JP)

( * ) Notice: Subject to any disclaimer, the term of this patent is extended or adjusted under 35 U.S.C. 154(b) by 127 days.

(21) Appl. No.: 16/189,647

(22) Filed: Nov. 13, 2018

(65) Prior Publication Data
US 2019/0062851 A1 Feb. 28, 2019

Related U.S. Application Data

(62) Division of application No. 15/034,592, filed as application No. PCT/JP2014/081448 on Nov. 27, 2014, now Pat. No. 10,161,011.

(30) Foreign Application Priority Data

Nov. 29, 2013 (JP) ................. 2013-248277

(51) Int. Cl.
C12Q 1/70 (2006.01)
(52) U.S. Cl.
CPC ....... *C12Q 1/701* (2013.01); *C12Q 2600/158* (2013.01)
(58) Field of Classification Search
CPC .............. C12Q 1/701; C12Q 2561/113; C12Q 2563/173; C12Q 2600/158
See application file for complete search history.

(56) References Cited

U.S. PATENT DOCUMENTS

| | | |
|---|---|---|
| 2004/0132046 A1 | 7/2004 | Westman et al. |
| 2011/0076744 A1 | 3/2011 | Wright et al. |
| 2013/0195801 A1 | 8/2013 | Gao et al. |
| 2014/0107186 A1 | 4/2014 | Garcia et al. |

FOREIGN PATENT DOCUMENTS

| | | |
|---|---|---|
| CN | 103114152 A | 5/2013 |
| JP | 2013-531471 A | 8/2013 |
| WO | WO 2012/123430 A1 | 9/2012 |

OTHER PUBLICATIONS

Aoyagi, "Real Time PCR," PCR Experimental Protocol Selected According to Purposes, Jan. 1, 2011, pp. 120-131, with partial English translation.

Aurnhammer et al., "Universal Real-Time PCR for the Detection and Quantification of Adeno-Associated Virus Serotype 2-Derived Inverted Terminal Repeat Sequences," Human Gene Therapy Methods: Part B, vol. 23, Feb. 2012 (Online Jun. 6, 2011), pp. 18-28 (Total 12 pages).
Chinese Office Action and Search Report for corresponding Chinese Application No. 201480065018.8, dated Jan. 17, 2018, with English translation.
Diao et al., "Biological Assay of Recombinant Adeno-Associated Virus Gene Medicine," Chin J New Drugs Clin Rem, vol. 29, No. 10, Oct. 2010, pp. 728-732 with partial English translation (15 pages total).
Extended European Search Report for corresponding European Application No. 14866486.5, dated May 15, 2017.
Hojo, "Real Time PCR," Experimental Medicine Separate Volume, Easy to Understand from Principle Series, Real-Time PCR Perfect Experimental Guidelines), Oct. 10, 2013, pp. 14-21, with partial English translation.
International Search Report (form PCT/ISA/210), dated Feb. 17, 2015, for International Application No. PCT/JP2014/081448, with English translation.
Meng et al., "Novel qPCR Strategy for Quantification of Recombinant Adeno-Associated Virus Serotype 2 Vector Genome-Titer," Chin J Biotech, vol. 29, No. 2, 2013, pp. 235-242 with partial English translation (10 pages total).
Takara, "AAVpro™ Helper Free System (AAV2)," Product Manual, retrieved from URL:http://www.clontech.com/ES/Products/Viral_Transduction/AAV_Vector_Systems/ibcGetAttachment.jsp? cItemId=93546&fileId=6846850&sitex=10023:22372:US, Nov. 28, 2011, XP-002769460, 18 pages.
Wang et al., "A Reliable and Feasible qPCR strategy for Titrating AAV Vectors," Medical Science Monitor Basic Research, vol. 19, Jul. 5, 2013, XP-002769459, pp. 187-193.
Lowe et al.; A computer program for selection of oligonucleotide primers for polymerase chain reactions; Nucleic Acids Research; (1990) vol. 18, No. 7, pp. 1757-1761.
Non-Final Office Action dated Jan. 5, 2018, issued in U.S. Appl. No. 15/034,592.
Non-Final Office Action dated Mar. 30, 2018, issued in U.S. Appl. No. 15/034,592.
Notice of Allowability dated Aug. 14, 2018, issued in U.S. Appl. No. 15/034,592.
Japanese Office Action for corresponding Japanese Application No. 2015-550997, dated Jan. 21, 2019.
Rohr et al., "Fast and Reliable Titration of Recombinant Adeno-Associated Virus Type-2 Using Quantitative Real-Time PCR," Journal of Virological Methods, vol. 106, 2002, pp. 81-88.

*Primary Examiner* — David C Thomas
(74) *Attorney, Agent, or Firm* — Birch, Stewart, Kolasch & Birch, LLP

(57) ABSTRACT

A method for quantification of an adeno-associated virus genome, including the steps of (a) preparing a composition containing a sample, at least one primer pair for use in amplification of only a nucleotide sequence contained in inverted terminal repeats of an adeno-associated virus, and an intercalating dye; (b) performing nucleic acid amplification reaction using the composition prepared in the step (a); and (c) detecting an amplified product obtained in the step (b). The present invention is especially useful in the fields of medicine, gene engineering, and biology.

4 Claims, 4 Drawing Sheets
Specification includes a Sequence Listing.

SEQUENCE LISTING

```
<160> NUMBER OF SEQ ID NOS: 13

<210> SEQ ID NO 1
<211> LENGTH: 21
<212> TYPE: DNA
<213> ORGANISM: Artificial Sequence
<220> FEATURE:
<223> OTHER INFORMATION: Designed PCR primer "L1"

<400> SEQUENCE: 1
aggaacccct agtgatggag t                                              21

<210> SEQ ID NO 2
<211> LENGTH: 20
<212> TYPE: DNA
<213> ORGANISM: Artificial Sequence
<220> FEATURE:
<223> OTHER INFORMATION: Designed PCR primer "L2"

<400> SEQUENCE: 2
aggaacccct agtgatggag                                                20

<210> SEQ ID NO 3
<211> LENGTH: 22
<212> TYPE: DNA
<213> ORGANISM: Artificial Sequence
<220> FEATURE:
<223> OTHER INFORMATION: Designed PCR primer "L3"
```

<400> SEQUENCE: 3 ggaacccta gtgatggagt tg                                    22

<210> SEQ ID NO 4
<211> LENGTH: 21
<212> TYPE: DNA
<213> ORGANISM: Artificial Sequence
<220> FEATURE:
<223> OTHER INFORMATION: Designed PCR primer "L4"

<400> SEQUENCE: 4 ggaacccta gtgatggagt t                                     21

<210> SEQ ID NO 5
<211> LENGTH: 23
<212> TYPE: DNA
<213> ORGANISM: Artificial Sequence
<220> FEATURE:
<223> OTHER INFORMATION: Designed PCR primer "L5"

<400> SEQUENCE: 5 ggaacccta gtgatggagt tgg                                   23

<210> SEQ ID NO 6
<211> LENGTH: 24
<212> TYPE: DNA
<213> ORGANISM: Artificial Sequence
<220> FEATURE:
<223> OTHER INFORMATION: Designed PCR primer "L6"

<400> SEQUENCE: 6
aggaacccct agtgatggag ttgg                                 24

<210> SEQ ID NO 7
<211> LENGTH: 17
<212> TYPE: DNA
<213> ORGANISM: Artificial Sequence
<220> FEATURE:
<223> OTHER INFORMATION: Designed PCR primer "R1"

<400> SEQUENCE: 7
cctcagtgag cgagcga                                         17

<210> SEQ ID NO 8
<211> LENGTH: 18
<212> TYPE: DNA
<213> ORGANISM: Artificial Sequence
<220> FEATURE:
<223> OTHER INFORMATION: Designed PCR primer "R2"

<400> SEQUENCE: 8
cctcagtgag cgagcgag                                        18

<210> SEQ ID NO 9
<211> LENGTH: 17
<212> TYPE: DNA
<213> ORGANISM: Artificial Sequence
<220> FEATURE:
<223> OTHER INFORMATION: Designed PCR primer "R3"

<400> SEQUENCE: 9
ggcctcagtg agcgagc                                         17

```
<210> SEQ ID NO 10
<211> LENGTH: 16
<212> TYPE: DNA
<213> ORGANISM: Artificial Sequence
<220> FEATURE:
<223> OTHER INFORMATION: Designed PCR primer "R4"

<400> SEQUENCE: 10
cggcctcagt gagcga                                                    16

<210> SEQ ID NO 11
<211> LENGTH: 17
<212> TYPE: DNA
<213> ORGANISM: Artificial Sequence
<220> FEATURE:
<223> OTHER INFORMATION: Designed PCR primer "R5"

<400> SEQUENCE: 11
gtcgcccggc ctcagtg                                                   17

<210> SEQ ID NO 12
<211> LENGTH: 16
<212> TYPE: DNA
<213> ORGANISM: Artificial Sequence
<220> FEATURE:
<223> OTHER INFORMATION: Designed PCR primer "R6"

<400> SEQUENCE: 12
tcgcccggcc tcagtg                                                    16

<210> SEQ ID NO 13
<211> LENGTH: 19
<212> TYPE: DNA
<213> ORGANISM: Artificial Sequence
<220> FEATURE:
<223> OTHER INFORMATION: Designed PCR primer "R7"

<400> SEQUENCE: 13
agcgagcgag cgcgcagag                                                 19
```

METHOD FOR QUANTIFYING ADENO-ASSOCIATED VIRUS

This application is a Divisional of U.S. application Ser. No. 15/034,592, filed May 5, 2016, which is the U.S. National Phase of PCT/JP2014/081448, filed Nov. 27, 2014, which claims priority under 35 U.S.C. 119(a) to Japanese Patent Application No. 2013-248277, filed Nov. 29, 2013, the contents of all of which are incorporated by reference, in their entirety, into the present application.

TECHNICAL FIELD

The present invention relates to a method for quantification of an adeno-associated virus (AAV) genome, a titer determination method of the AAV, a composition for use in quantification of the AAV genome, a kit for quantification of the AAV genome, a method for quantification of the AAV, a composition for use in quantification of the AAV, and a kit for quantification of the AAV.

BACKGROUND ART

Adeno-associated viruses (AAVs) are linear, single-stranded DNA viruses that belong to the Parvovirus family. The AAVs are infectious to cells of a wide range of species including human, and also infect non-dividing cells in which differentiation is terminated such as blood cells, muscles, or neural cells. Wild-type AAVs are not pathogenic to human. Also, the AAV particles are very stable physicochemically. From these features, the development of AAVs as vectors for gene transduction has been progressed.

The AAV particles comprise protein capsid having three capsid proteins (VP1, VP2, and VP3) and a single-stranded DNA genome surrounded therewith. The genome of the wild-type AAVs has a nucleotide sequence forming a T-shaped hairpin structure called ITR (Inverted Terminal Repeat) at both terminals, and a half of the linear single-stranded genome between the terminals encodes Rep protein (rep gene), and the remainder half encodes a capsid protein (cap gene). At least thirteen serotypes (AAV 1-13) have been known to date as wild-type AAVs which are infectious to human.

Typical recombinant adeno-associated viral vectors (rAAV vectors) have a genome structure in which rep gene and cap gene of the AAV genome are replaced with desired genes and the like. One example of the method for preparing an rAAV vector includes a method including introducing into host cells such as 293 cells collectively a vector plasmid in which an intended gene is inserted between ITRs at both terminals of the AAV, a helper plasmid for supplying a viral protein in need of replication of the AAV or formation of viral particles, and an adenovirus helper plasmid having a part of gene region serving as a helper action of the adenovirus in need of proliferation of the AAV, to produce an rAAV vector in the nucleus of the host cells. When the rAAV vector is used for gene transduction of the cells, it is necessary to prepare an rAAV vector having a sufficiently high titer. Therefore, the determination of the titer is essential in the preparation of the rAAV vector.

As the determination method for titer of rAAV, southern blotting method, dot blotting method, and real-time PCR method or the like has been utilized. Among them, it is said that it is preferable to utilize the real-time PCR method, from the viewpoint of convenience and rapidness of the operation, or the like. The ITR of the rAAV vector has a secondary structure which is difficult to perform PCR amplification. Therefore, as a target sequence for the determination according to real-time PCR of the titer of the rAAV vector, a foreign gene inserted into the vector has been utilized. However, when a foreign gene is utilized as the target sequence, it is necessary to design primers utilized in PCR for every vector constructed. Recently, a report has been made on a determination method for titer of an rAAV vector according to real-time PCR using a TaqMan probe, in which the ITR sequence alone is a target sequence (Non-Patent Publication 1). However, it is necessary to synthesize a double labeled nucleic acid probe in the real-time PCR using the TaqMan probe, so that it is more costly as compared to quantitative real-time PCR using an intercalating dye.

PRIOR ART REFERENCES

Non-Patent Publications

Non-Patent Publication 1: *Human Gene Therapy Methods*, February 2012, Part B 23, 18-28

SUMMARY OF THE INVENTION

Problems to be Solved by the Invention

Accordingly, an object of the present invention is to provide a method for quantification of adeno-associated virus (AAV) which is convenient and highly efficient, a titer determination method of AAV, a method for quantification of the AAV genome, a composition for use in quantification of the AAV, a composition for use in quantification of the AAV genome, a kit for quantification of the AAV, and a kit for quantification of the AAV genome.

Means to Solve the Problems

As a result of intensive efforts in order to solve the problems mentioned above, the present inventors have found that quantification of the AAV genome is made possible according to quantitative real-time PCR using an intercalating dye with an ITR sequence alone as a target sequence. The present invention has been perfected thereby.

In other words, the present invention relates to the following [1] to [13]:

[1] A method for quantification of an adeno-associated virus genome, including the steps of:

(a) preparing a composition containing a sample, at least one primer pair for use in amplification of only a nucleotide sequence contained in inverted terminal repeats of an adeno-associated virus, and an intercalating dye;

(b) performing nucleic acid amplification reaction using the composition prepared in the step (a); and (c) detecting an amplified product obtained in the step (b).

[2] The method according to [1], wherein the primer pair consists of a primer containing a nucleotide sequence as shown in SEQ ID NO: 1 of the Sequence Listing, and a primer containing a nucleotide sequence as shown in SEQ ID NO: 7 of the Sequence Listing.

[3] The method according to [1] or [2], wherein the primer pair consists of a primer consisting of a nucleotide sequence as shown in SEQ ID NO: 1 or 2 of the Sequence Listing, and a primer consisting of a nucleotide sequence as shown in SEQ ID NO: 7 or 8 of the Sequence Listing.

[4] The method according to any one of [1] to [3], wherein the intercalating dye contains a cyanine-based dye.
[5] A titer determination method of an adeno-associated virus, including the step of quantifying an adeno-associated virus genome according to a method as defined in any one of [1] to [4].
[6] A composition for quantification of an adeno-associated virus genome, the composition containing at least one primer pair for use in amplification of only a nucleotide sequence contained in inverted terminal repeats of an adeno-associated virus, and an intercalating dye.
[7] The composition according to [6], wherein the primer pair consists of a primer containing a nucleotide sequence as shown in SEQ ID NO: 1 of the Sequence Listing, and a primer containing a nucleotide sequence as shown in SEQ ID NO: 7 of the Sequence Listing.
[8] The composition according to [6] or [7], wherein the primer pair consists of a primer consisting of a nucleotide sequence as shown in SEQ ID NO: 1 or 2 of the Sequence Listing, and a primer consisting of a nucleotide sequence as shown in SEQ ID NO: 7 or 8 of the Sequence Listing.
[9] The composition according to any one of [6] to [8], wherein the intercalating dye contains a cyanine-based dye.
[10] A kit for quantification of an adeno-associated virus genome, the kit containing a DNA polymerase, at least one primer pair for use in amplification of only a nucleotide sequence contained in inverted terminal repeats of an adeno-associated virus, and an intercalating dye.
[11] The kit according to [10], wherein the primer pair consists of a primer containing a nucleotide sequence as shown in SEQ ID NO: 1 of the Sequence Listing, and a primer containing a nucleotide sequence as shown in SEQ ID NO: 7 of the Sequence Listing.
[12] The kit according to [10] or [11], wherein the primer pair consists of a primer consisting of a nucleotide sequence as shown in SEQ ID NO: 1 or 2 of the Sequence Listing, and a primer consisting of a nucleotide sequence as shown in SEQ ID NO: 7 or 8 of the Sequence Listing.
[13] The kit according to any one of [10] to [12], wherein the intercalating dye contains a cyanine-based dye.

Here, as the cyanine-based dye used in the present invention, [2-[N-(3-dimethylaminopropyl)-N-propylamino]-4-[2,3-dihydro-3-methyl-(benzo-1,3-thiazol-2-yl)-methylidene]-1-phenyl-quinolinium] represented by the following formula (I) of CAS Registration No. 163795-75-3, or a salt thereof can be used. In other words, N',N'-dimethyl-N-[4-[(E)-(3-methyl-1,3-benzothiazol-2-ylidene)methyl]-1-phenylquinolin-1-ium-2-yl]-N-propylpropane-1,3-diamine, or a salt thereof can be used. These are called SYBR(registered trademark) Green I. Further, the cyanine-based dye may be a cis-trans isomer, and N',N'-dimethyl-N-[4-[(Z)-(3-methyl-1,3-benzothiazol-2-ylidene)methyl]-1-phenylquinolin-1-ium-2-yl]-N-propylpropane-1,3-diamine represented by the following formula (II), or a salt thereof can be used.

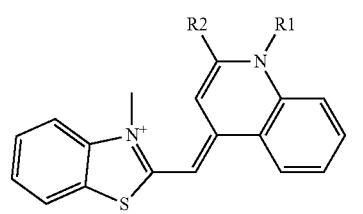
(I)

wherein R1 is:

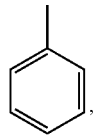
, and
R2 is:

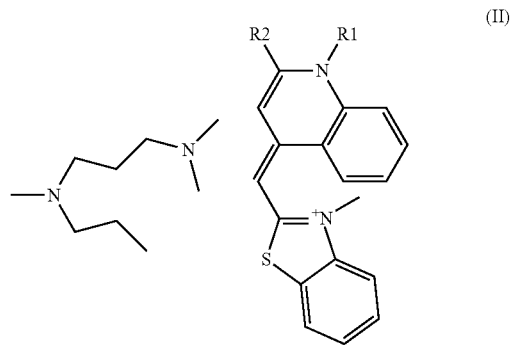
(II)

wherein R1 is:

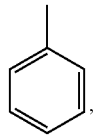
, and
R2 is:

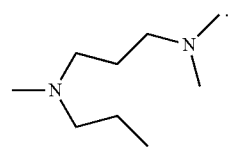

Effects of the Invention

According to the present invention, a method for quantification of adeno-associated virus (AAV) which is convenient and highly efficient, a titer determination method of the AAV, a method for quantification of the AAV genome, a composition for use in quantification of the AAV, a composition for use in quantification of the AAV genome, a kit for use in quantification of the AAV, and a kit for use in quantification of the AAV genome can be provided.

MODES FOR CARRYING OUT THE INVENTION

Figure 1:
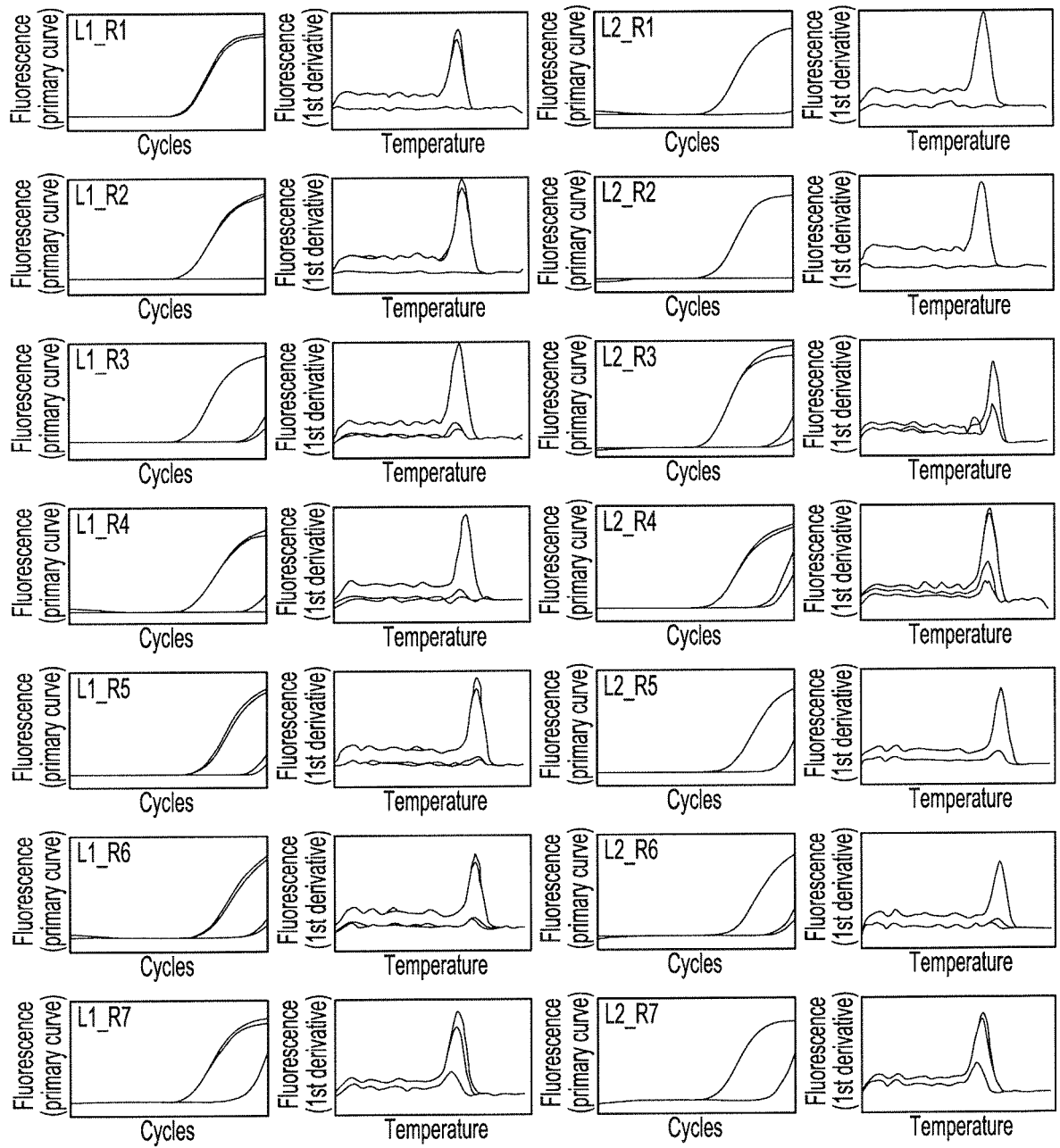
FIG. 1 Charts showing amplification curves and the analytical results of melting curves obtained by real-time PCR in Example 3, wherein L1_R1 in the figure shows a reaction in which a primer L1 and a primer R1 are used as a primer pair.

The method for quantification of adeno-associated virus genome of the present invention includes the steps of
(a) preparing a composition containing a sample, at least one primer pair for use in amplification of only a nucleotide sequence contained in inverted terminal repeats of an adeno-associated virus, and an intercalating dye;
(b) performing nucleic acid amplification reaction using the composition prepared in the step (a); and
(c) detecting an amplified product obtained in the step (b).

The method of the present invention is applicable to adeno-associated virus (AAV) genome of any of known serotypes, which can be utilized, for example, in quantification of at least one AVV genome selected from the group consisting of AAV1, AAV2, AAV3, AAV4, AAV5, AAV6, AAV7, AAV8, AAV9, AAV10, AAV11, AAV12, and AAV13. The AAV in the method of the present invention includes, but not particularly limiting the present invention thereto, recombinant adeno-associated viral vectors (rAAV vectors). Here, when the serotypes of the rAAV vectors are mentioned herein, the serotypes derived from capsid are used as standards. In other words, the serotypes of the rAAV vectors are assumed to be determined according to the origin of cap gene used in the preparation of the rAAV, and are assumed to be independent from the derivation of serotypes of AAV genome that are included in the rAAV particles. For example, in a case where capsid is derived from AAV6, and ITRs in the AVV genome included in the rAAV particles are derived from AAV2, the rAAV vector is assumed to be serotype 6 in the present specification.

The method for quantification of an AAV genome of the present invention can be used in quantification of the AAV. Therefore, the method for quantification of AAV utilizing the method for quantification of AAV genome of the present invention is one of preferred embodiments in the present invention. The original amount of AAV can be deduced by allowing a DNA outside of the AAV particles in a composition containing AAV to degrade or remove, then liberating a genomic DNA from the AAV particles, and quantifying this genomic DNA according to the method for quantification of an AAV genome of the present invention. A titer determination method for rAAV vector which is carried out by determining the amount of an AAV as described above is similarly one of preferred embodiments of the present invention. Here, the titer of AAV deduced by quantification of the AAV genome may be also referred to as genome titer. The rAAV vector may be derived from different serotypes of AAVs for genomic DNA and capsid. For example, according to the method of the present invention, the titer of rAAV vector having a genomic DNA carrying ITR derived from AAV2 and a foreign gene inserted in the internal thereof and having capsid derived from AAV of serotypes other than AAV2, can be determined.

The samples in the method of the present invention include samples obtained through the steps of liberating a genomic DNA of AAV from samples in which AAV is present, or samples that are needed to be confirmed of the presence or absence of AAV. The above samples include a composition obtained through the steps of extracting AAV produced in host cells from the host cells, or culture supernatant of cells producing AAV, and preferably include a composition containing rAAV vector obtained through the step of extracting rAAV vector from rAAV vector producing cells, or culture supernatant of rAAV vector producing cells.

The method for extracting AAV from host cells, for example, a method for extracting an rAAV vector from an rAAV vector producing cells includes, but not particularly limiting the present invention thereto, for example, a freeze-thawing method, a sonication disruption method, and a solution extraction method. The solution extraction method includes a method of contacting host cells with an acidic solution. The method of contacting host cells with an acidic solution may be carried out by suspending host cells harvested by centrifugation or filtration in an acidic solution, or adding a component that is capable of making culture medium containing host cells acidic to the culture medium. The pH of the acidic solution includes, for example, a pH of from 3.0 to 6.9, preferably a pH of from 3.0 to 6.0, and more preferably a pH of from 3.0 to 5.0. In addition, the acidic solution includes, but not particularly limiting the present invention thereto, solutions containing at least one member selected from the group consisting of citric acid, acetic acid, malic acid, phosphoric acid, hydrochloric acid, sulfuric acid, nitric acid, lactic acid, propionic acid, butyric acid, oxalic acid, malonic acid, succinic acid, fumaric acid, maleic acid, tartaric acid, benzoic acid, sulfosalicylic acid, formic acid, and salts thereof, and Good buffers having a buffering region at a pH of less than 7, such as MES and Bis-Tris, and in the present invention, preferably including citric acid, acetic acid, phosphoric acid, and salts thereof, and more preferably including citric acid among them.

The time for contacting host cells with an acidic solution includes, but not particularly limiting the present invention thereto, for example, from 1 minute to 48 hours, and preferably from 5 minutes to 24 hours. The temperature conditions upon contacting host cells with an acidic solution include, for example, from 0 to 40° C., and preferably from 4 to 37° C. The AVV extract which is extracted from host cells may contain a DNA derived from host cells. For example, the AVV extract may be subjected to a treatment with deoxyribonuclease, and this DNA may be degraded.

In order to liberate a genomic DNA from AVV, a known method that allow breakdown of capsid of AVV may be utilized, which includes, for example, a method of treating AAV with a solution containing a protein denaturant or surfactant, thereby liberating a genomic DNA, and a method of allowing breakdown of capsid of AAV by heat treatment. The solution containing a liberated AAV genome thus prepared can be used as a sample in the method for quantification of AAV of the present invention.

At least one primer pair for use in amplification of only a nucleotide sequence contained in inverted terminal repeats of the adeno-associated virus in the method of the present invention is not particularly limited, so long as the primer pair is capable of quantification of the genomic DNA of AAV vector by using a quantitative nucleic acid amplification reaction utilizing an intercalating dye. When the method of the present invention is utilized in quantification of the genomic DNA of rAAV vector, the primer pair is, but not particularly limiting the present invention thereto, preferably at least one primer pair for use in amplification of only a nucleotide sequence containing ITRs of AAV, which is at least one member selected from the group consisting of AAV1, AAV2, AAV3, AAV6 and AAV7.

The primer pair as mentioned above preferably includes, for example,
a primer pair consisting of a primer consisting of a nucleotide sequence as shown in SEQ ID NO: 1 and a primer consisting of a nucleotide sequence as shown in SEQ ID NO: 7,
a primer pair consisting of a primer consisting of a nucleotide sequence as shown in SEQ ID NO: 1 and a primer consisting of a nucleotide sequence as shown in SEQ ID NO: 8,
a primer pair consisting of a primer consisting of a nucleotide sequence as shown in SEQ ID NO: 2 and a primer consisting of a nucleotide sequence as shown in SEQ ID NO: 7, and
a primer pair consisting of a primer consisting of a nucleotide sequence as shown in SEQ ID NO: 2 and a primer consisting of a nucleotide sequence as shown in SEQ ID NO: 8.
These primers are designed based on ITR sequences derived from AAV2 and AAV6, and the primers can be used in quantification of AAV genomes of AAV1, AAV2, AAV3, AAV6 and AAV7, or genomes of rAAV vector having ITRs derived from AAV of these serotypes. From the viewpoint of the correlation between Ct values and amounts of template calculated by real-time PCR, the range of the amounts of template for obtaining high correlation, and amplification efficiency of PCR, the primer pair more preferably includes a primer pair consisting of a primer consisting of a nucleotide sequence as shown in SEQ ID NO: 1 of the Sequence Listing and a primer consisting of a nucleotide sequence as shown in SEQ ID NO: 7 of the Sequence Listing. The amount of each primer used in the nucleic acid amplification reaction in the method of the present invention includes, but not limiting the present invention thereto, from 0.5 to 15 pmol, preferably from 1 to 10 pmol, and more preferably from 2 to 8 pmol, for example, 5 pmol, per 25 µL of the reaction solution of the nucleic acid amplification reaction.

The intercalating dye as used herein refers to a dye of which fluorescence is enhanced by intercalation to double-stranded nucleic acids. The intercalating dye in the present invention is not particularly limited thereto, and any dyes which enhance fluorescence by intercalation to nucleic acids are embraced by the intercalating dyes in the present invention. The dye includes, but not particularly limited thereto, for example, ethidium bromide and a cyanine-based dye. The above cyanine-based dye includes SYBR(registered trademark) Green I, PicoGreen, YOYO, TOTO, SYTO9, LCGreen, EvaGreen, and analogues thereof, and the like.

Among them, the intercalating dye in the method of the present invention is preferably SYBR(registered trademark) Green I.

SYBR(registered trademark) Green I is an asymmetric cyanine-based dye, of which structure is elucidated by Zipper H et al. (*Nucleic Acids Research*, 2004, 32(12), e103). In the publication, it is analyzed as [2-[N-(3-dimethylaminopropyl)-N-propylamino]-4-[2,3-dihydro-3-methyl-(benzo-1,3-thiazol-2-yl)-methylidene]-1-phenyl-quinolinium] represented by the following formula (I), or a salt thereof. In other words, it is N',N'-dimethyl-N-[4-[(E)-(3-methyl-1,3-benzothiazol-2-ylidene)methyl]-1-phenylquinolin-1-ium-2-yl]-N-propylpropane-1,3-diamine or a salt thereof. These are called SYBR(registered trademark) Green I. Further, the dye may be a cis-trans isomer of the compound represented by the above formula (I), and N',N'-dimethyl-N-[4-[(Z)-(3-methyl-1,3-benzothiazol-2-ylidene)methyl]-1-phenylquinolin-1-ium-2-yl]-N-propylpropane-1,3-diamine represented by the following formula (II), or a salt thereof can also be used.

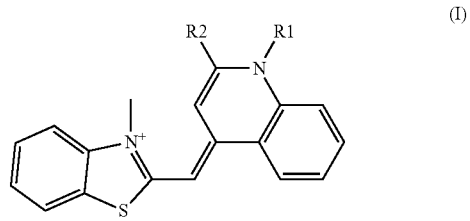

wherein R1 is:

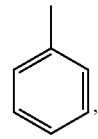

and
R2 is:

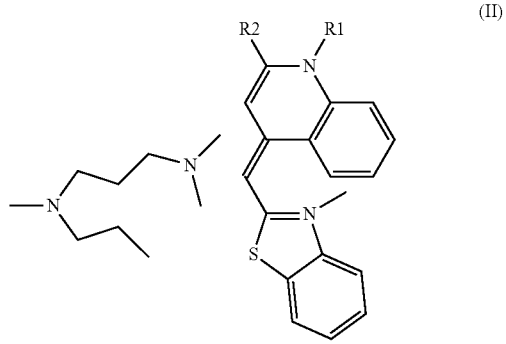

wherein R1 is:

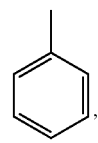

and

R2 is:

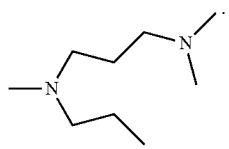

According to Zipper H et al., SYBR(registered trademark) Green I sold by Life Technologies, which is a molar concentration of a 10,000-fold dilution (×1 concentration) of SYBR(registered trademark) Green I in a DMSO solution of SYBR (registered trademark) Green I is about 2 µM. The concentration of the intercalating dye suitable for quantitative nucleic acid amplification reaction can be appropriately determined by one of ordinary skill in the art referring to the known information, and the concentration includes, for example, ×0.025 concentration (about 50 nM) or more, preferably from ×0.05 concentration (about 100 nM) to ×2 concentration (about 4 µM), and more preferably from ×0.1 concentration (about 200 nM) to ×1 concentration (about 2 µM).

The nucleic acid amplification reaction utilizable in the method of the present invention includes, but not particularly limiting the present invention thereto so long as the reaction synthesizes a DNA complementary thereto with a DNA as a template, for example, nucleic acid amplification reactions that are well known in the art, such as polymerase chain reaction (PCR), ICAN, LAMP, and SDA, and preferably includes PCR among them.

In a case where PCR is utilized in the method of the present invention, general conditions can be applied as the conditions of temperature cycles for PCR. PCR is carried out by, for example, a reaction comprising three steps of dissociating double-stranded template DNA to single strand (denaturation), annealing a primer to the single-stranded template DNA, and synthesizing a complementary strand from the primer (extension), or a reaction comprising a two-step reaction, in which the annealing and the extension of the primer among the three-step reaction mentioned above are carried out at the same temperature, referred to as "shuttle PCR" ["*PCR Ho Saizensen (Front Line of PCR Method)*," "*(Tanpakushitsu Kakusan Koso (Proteins, Nucleic Acids and Enzymes)" Supplement*, 41(5), 425 to 428 (1996)]. The temperature cycles for PCR are, but not particularly limiting the present invention thereto, less than 40 cycles, and, for example, preferably 35 cycles or so, in order to avoid the production of nonspecific amplified products. The temperature cycles include, but not particularly limited hereto, treatment at 95° C. for 2 minutes, and thereafter 35 cycles of reactions, one cycle comprising 95° C. for 5 seconds, and 60° C. for 30 seconds.

The amplified products obtained by the nucleic acid amplification reaction in the method of the present invention can be detected by determining a fluorescent intensity of the intercalating dye. The determination of a fluorescent intensity of the intercalating dye may be carried out in the process of the step of performing a nucleic acid amplification reaction, in this case, the nucleic acid amplification process can be monitored. In the monitoring of the nucleic acid amplification process, for example, a commercially available apparatus for real-time PCR, for example, Thermal Cycler Dice(registered trademark) Real Time System II (manufactured by TAKARA BIO INC.) may be used.

In the quantification of DNA utilizing the monitoring results of the nucleic acid amplification process, a known method in the art may be utilized. Although not particularly limiting the present invention thereto, for example, a serially diluted standard DNAs (positive control DNA) having nucleotide sequences that serve as a template for nucleic acid amplification according to a primer pair used in a nucleic acid amplification reaction are prepared, Ct values are calculated according to real-time PCR in which the dilution series are used as a template, to draw a calibration curve, and DNA in the sample can be quantified based on the curve. As the above standard nucleic acids, for example, plasmid DNA can be used. As the method for calculating Ct values, for example, a method in which an intersecting point of a threshold and amplification curve is defined as a Ct value (Crossing Point method), or a method in which a second derivative function of an amplification curve is obtained, and a point at which the second derivative is at maximum is defined as a Ct value (2nd Derivative Maximum method) can be utilized.

The method of the present invention may include the step of further performing melting curve analysis. In the melting curve analysis, the temperature of the reaction mixture after the nucleic acid amplification reaction is gradually increased, and fluorescent signals of an intercalating dye are monitored during the temperature rise. The nucleic acid amplified products form a double strand and show intensive fluorescent signals at low temperatures, but they dissociate to a single strand upon reaching a certain temperature, where the intensity of fluorescent signals of the intercalating dye is drastically lowered. The temperature at this time is a melting temperature (Tm value). According to the melting curve analysis, the Tm values of amplified products can be examined to confirm whether or not the amplified products are specific amplified products.

The composition for use in quantification of the adeno-associated virus genome of the present invention contains at least one primer pair for use in amplification of only a nucleotide sequence contained in inverted terminal repeats of the adeno-associated virus, and an intercalating dye, which can be utilized for carrying out the method of the present invention. The composition of the present invention may further contain at least one member selected from the group consisting of DNA polymerases, reaction buffers, divalent metal ions, and deoxyribonucleotide triphosphates.

The DNA polymerase used in the present invention is not particularly limited, so long as the polymerase has an activity of synthesizing a DNA complementary thereto with a DNA as a template. Although not particularly limiting the present invention thereto, the DNA polymerase used in the present invention is preferably a thermostable DNA polymerase. The DNA polymerase as mentioned above includes thermostable DNA polymerase derived from eubacteria such as DNA polymerase derived from bacteria belonging to the genus *Thermus* (DNA polymerase derived from *Thermus aquaticus*, etc.), and DNA polymerase derived from thermophilic bacteria belonging to the genus *Bacillus* (DNA polymerase derived from *Bacillus caldotenax* etc.); and thermostable DNA polymerase derived from archaebacteria such as DNA polymerase derived from archaebacteria belonging to the genus *Pyrococcus* (DNA polymerase derived from *Pyrococcus* sp., etc.) and DNA polymerase derived from archaebacteria belonging to the genus *Thermococcus* (DNA polymerase derived from *Thermococcus kodakaraensis* etc.). In addition, the DNA polymerase of any of naturally occurring enzymes and recombinant enzymes can be used in the present invention, and DNA polymerase in which a naturally occurring amino acid sequence is modified within the range of having DNA polymerase activity can also be used in the present invention.

The composition of the present invention may contain two or more kinds of DNA polymerases. The two or more kinds of DNA polymerases include a combination of DNA polymerase possessing 3'→5' exonuclease activity and DNA polymerase not essentially possessing 3'→5' exonuclease activity. Here, the technique of performing PCR with a reaction mixture containing two kinds of DNA polymerases as mentioned above is known as LA-PCR (Long and Accurate PCR). Although not particularly limiting the present invention thereto, in the present invention, the combination of DNA polymerase possessing 3'→5' exonuclease activity and DNA polymerase not essentially possessing 3'→5' exonuclease activity is preferred.

The concentration of the DNA polymerase in the composition of the present invention is not particularly limited so long as the concentration is a concentration at which DNA synthesis reaction can be performed, and the concentration includes, for example, a concentration at which PCR can be performed. In a case where PCR is carried out with 25 µL of a reaction mixture using DNA polymerase derived from *Thermus aquaticus*, the amount of the DNA polymerase in the reaction mixture may be adjusted to from 0.125 to 5 U or so. Here, the activity of the thermostable DNA polymerase described herein is based on the indications of commercially available enzymes, and, for example, an activity for incorporating 10 nmol of all the nucleotides in an acid-insoluble precipitation in a reaction mixture for activity determination (25 mM TAPS Buffer (pH 9.3, 25° C.), 50 mM KCl, 2 mM $MgCl_2$, 1 mM 2-Mercaptoethanol, 200 µM each of dATP, dGTP, and dTTP, 100 µM [$\alpha$-$^{32}$P] dCTP, 0.25 mg/mL activated salmon sperm DNA) at 74° C. for 30 minutes using activated salmon sperm DNA as a template/primer is defined as 1 U.

The reaction buffer as used herein refers to a compound or mixture having an action of moderating the fluctuation of a hydrogen ion concentration (pH) of the reaction solution. In general, since a mixed solution of a weak acid or a salt thereof, or a weak base or a salt thereof has a strong buffering action, the mixed solution has been widely used as reaction buffers for the purpose of pH control. Although not particularly limiting the present invention thereto, the pH of the composition of the present invention is appropriately set to an ordinary range at which PCR is carried out, for example, a range of a pH of from 8.0 to 9.5.

The divalent metal ions contained in the composition of the present invention include magnesium ions, manganese ions, and cobalt ions. The divalent metal ions and concentrations thereof suitable for each of DNA polymerases are well known in the art. The divalent metal ions may be supplied in the form of a salt such as a chloride, a sulfate, or an acetate. Although not particularly limiting the present invention thereto, the concentration of the divalent metal ion in the composition of the present invention includes, for example, from 0.5 to 20 mM.

The deoxyribonucleotide is a compound in which a phosphate group is bound to deoxyribose bound to an organic base via a phosphodiester bridge. Four kinds of deoxyribonucleotides each having adenine, guanine, cytosine, and thymine bases are found in naturally occurring DNA. The adenine, guanine, cytosine, and thymine bases are abbreviated as A, G, C, and T in many cases, respectively. The deoxyribonucleotide includes liberated monophosphate type, diphosphate type, and triphosphate type (in other words, having a phosphate moiety which has one, two, or three phosphate groups, respectively). In addition, it has been known that deoxyribonucleoside triphosphate of which base moiety has hypoxanthine or uracil can be used in nucleic acid amplification reaction. In the composition of the present invention, at least one member of deoxyribonucleoside triphosphate (for example, dATP, dCTP, dITP, dGTP, dTTP, and dUTP) and derivatives thereof can be used. The deoxyribonucleoside triphosphate which can be contained in the composition of the present invention includes preferably a mixture of dATP, dCTP, dGTP, and dTTP (or dUTP).

The kit for quantification of an adeno-associated virus of the present invention contains DNA polymerase, at least one primer pair for use in amplification of only a nucleotide sequence contained in inverted terminal repeats of the adeno-associated virus, and an intercalating dye. The DNA polymerase, at least one primer pair for use in amplification of only a nucleotide sequence contained in inverted terminal repeats of the adeno-associated virus, and an intercalating dye may be contained in the kit in the state where a part or all of them are mixed, or may be included in the kit in the state where each is a single component.

The kit of the present invention may further contain at least one member selected from the group consisting of reaction buffers, divalent metal ions, deoxyribonucleotide triphosphates, reagents for use in extraction of AAV from host cells, reagents for use in degradation or removal of DNA outside of viral particles of AAV, reagents for use in liberation of AAV genome from AAV, reagents for use in dilution of a DNA solution, and positive control DNAs for drawing calibration curve.

The reagent for use in extraction of AAV from the above host cells includes, but not limiting the present invention thereto, an acidic solution having a pH of from 3.0 to 6.9, preferably a pH of from 3.0 to 6.0, and more preferably a pH of from 3.0 to 5.0. In addition, the acidic solution includes, but not particularly limiting the present invention thereto, solutions containing at least one member selected from the group consisting of citric acid, acetic acid, malic acid, phosphoric acid, hydrochloric acid, sulfuric acid, nitric acid, lactic acid, propionic acid, butyric acid, oxalic acid, malonic acid, succinic acid, fumaric acid, maleic acid, tartaric acid, benzoic acid, sulfosalicylic acid, formic acid, and salts thereof, and Good buffers having a buffering region at a pH of less than 7, such as MES and Bis-Tris. In the present invention, among them, citric acid, acetic acid, phosphoric acid, and salts thereof are preferably included, and citric acid is more preferably included.

The above reagent for use in degradation or removal of DNA outside of viral particles of AAV includes, for example, deoxyribonuclease (DNase), such as DNase I. When the DNase is utilized as a reagent for use in degradation or removal of DNA outside of viral particles of AAV, the kit of the present invention may further contain a reaction buffer for the DNase.

The above reagent for use in liberation of AAV genomic DNA from particles of AAV includes, for example, a solution containing a protein denaturant or surfactant.

The above positive control DNA for drawing calibration curve includes nucleic acids containing nucleotide sequences that are capable of performing nucleic acid amplification with a primer pair contained in the kit of the present invention. The nucleic acids as mentioned above include, for example, plasmid DNAs.

EXAMPLES

The present invention will be described more specifically by means of Examples set forth below, without intending to restrict the scope of the present invention to the following Examples. Here, as the reactor for real-time PCR in the following Examples, Thermal Cycler Dice(registered trademark) Real Time System II (manufactured by TAKARA BIO INC.) was used.

Example 1 Design of Primer

A 5'-end primer and a 3'-end primer were designed against ITR of AAV type 2 (hereinafter, AAV2), based on the information of the genome nucleotide sequence (Ref Seq Acc. No. NC 001401) of AAV2. There are six kinds of 5'-end primers: L1 (SEQ ID NO: 1), L2 (SEQ ID NO: 2), L3 (SEQ ID NO: 3), L4 (SEQ ID NO: 4), L5 (SEQ ID NO: 5), and L6 (SEQ ID NO: 6), and seven kinds of 3'-end primers: R1 (SEQ ID NO: 7), R2 (SEQ ID NO: 8), R3 (SEQ ID NO: 9), R4 (SEQ ID NO: 10), R5 (SEQ ID NO: 11), R6 (SEQ ID NO: 12), and R7 (SEQ ID NO: 13).

Example 2 Preparation of Crudely Purified Genome Derived from rAAV2 Vector (1) Seeding of Cells for Producing rAAV2 Vector 293 Cells suspended in a DMEM (manufactured by Sigma) containing 10% FBS (manufactured by GIBCO) were seeded in a 10 cm dish for cell culture (manufactured by Corning). Thereafter, the cells were cultured overnight with a $CO_2$ incubator at 37° C., and it was confirmed that the cells were nearly 70% confluent.

(2) Transfection of Plasmid for Producing rAAV2 Vector

The cells prepared in Example 2-(1) mentioned above were transfected with a plasmid encoding Rep protein and Cap protein of AAV2, a plasmid harboring E2A, VA, and V4 sequences of adenovirus, and a plasmid harboring an expression cassette of a fluorescent protein ZsGreen1 between two ITRs of AAV2, using a calcium phosphate method. After the cells were transfected for 7 hours, the medium was completely removed, and DMEM containing 10% FBS was then added in a volume of 15 mL per dish, and the cells were cultured for 2 days in a $CO_2$ incubator at 37° C.

(3) Harvesting of rAAV2 Vector-Producing Cells

After the termination of the culture of (2), 3 mL of a PBS solution containing 20 mM EDTA was added to each dish, and reacted at room temperature for several minutes, to remove the cells. Thereafter, the cells were harvested together with the solution, and centrifuged at 4° C. at 1,750×g for 10 minutes, and then the supernatant was removed. An acidic buffer containing citric acid was added to the cell pellets, the mixture was centrifuged, and the supernatant thereof was called an rAAV2 vector extract. The nucleic acids outside the viral particles of AAV2 in the rAAV2 vector extract obtained was digested with DNase I, and a genomic DNA was then liberated from the AAV2 particles using a protein denaturant. The solution thus obtained was referred to as a crudely purified genomic solution derived from an rAAV2 vector.

Example 3 Screening for Primer Pair Selection

The six kinds of 5'-end primers and the seven kinds of 3'-end primers designed in Example 1 were combined to give primer pairs (a total of 42 combinations), and primer pairs that were effective in quantification of the AAV genome were screened. When screening, SYBR(registered trademark) Premix Ex Taq II(Tli RNaseH Plus) (manufactured by TAKARA BIO INC.) was used, and the screening was carried out with the following reaction composition. The amount 12.5 µL of SYBR(registered trademark) Premix Ex Taq II (Tli RNaseH Plus) (2×conc.), 0.5 µL of each 10 µM primer mix, and 5.0 µL of a template were mixed, and sterile water was added thereto to make up a total volume of 25 µL. As the template, the crudely purified genome solution derived from an rAAV2 vector prepared in Example 2 was used as the positive control. A reaction mixture having the same reaction composition except for using sterile water in place of the template was prepared, and used as a negative control. The reactions were performed in two runs for every primer pair, together with the negative control and the positive control. The reactions and the detection were performed according to real-time PCR, which comprised 95° C. for 2 minutes (initial denaturation), and thereafter 35 cycles of reactions, in which one cycle of reaction comprised 95° C. for 5 seconds and 60° C. for 30 seconds, using Thermal Cycler Dice(registered trademark) Real Time System II. In addition, after the termination of PCR, the melting curve analysis was performed.

Figure 2:
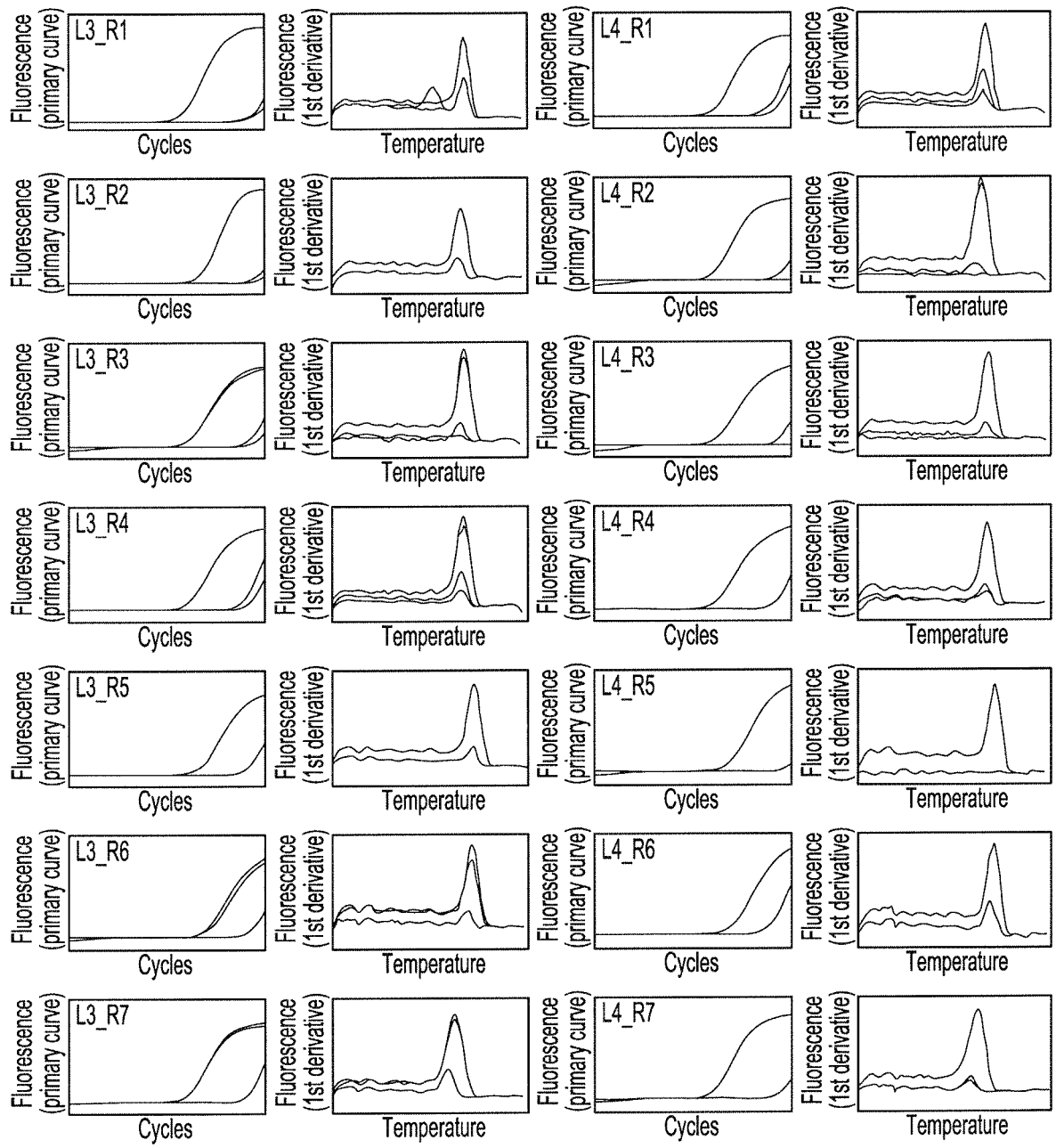
FIG. 2 Charts showing amplification curves and the analytical results of melting curves obtained by real-time PCR in Example 3, wherein L3_R1 in the figure shows a reaction in which a primer L3 and a primer R1 are used as a primer pair.
Figure 3:
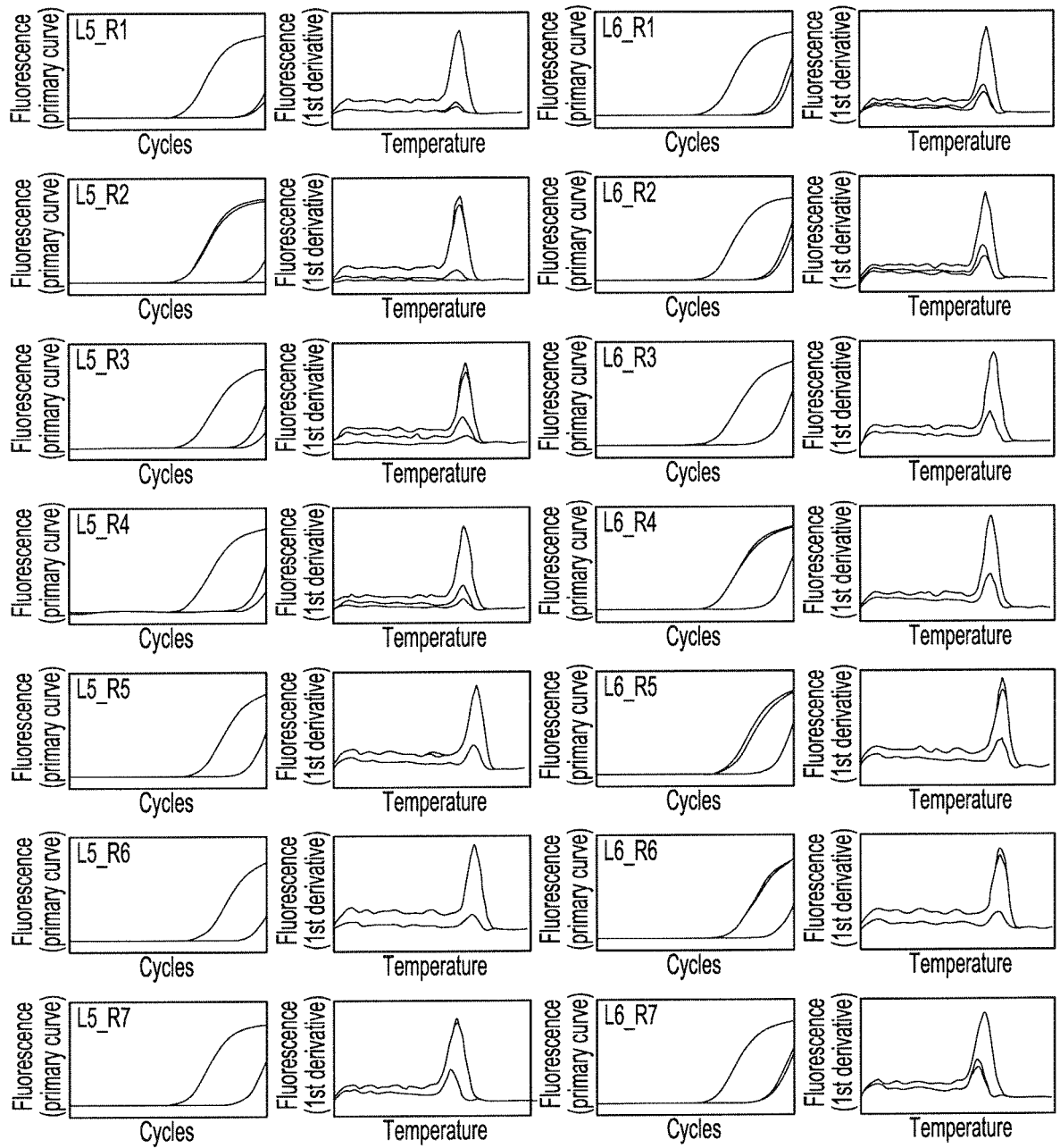
FIG. 3 Charts showing amplification curves and the analytical results of melting curves obtained by real-time PCR in Example 3, wherein L5_R1 in the figure shows a reaction in which a primer L5 and a primer R1 are used as a primer pair.

The amplified curves and the analytical results of melting curves obtained by real-time PCR summarized for every primer pair are shown in FIGS. 1, 2, and 3. In addition, based on the results, the judgments conducted on each primer pair for the reactivity in the positive control are shown in Table 1, and the judgments conducted on each primer pair for the presence or absence of nonspecific amplification in the negative control are shown in Table 2. In Table 1, "○" stands for combinations which are found to have excellent amplification signals, and "x" stands for combinations which are not found to be so. In Table 2, "○" stands for combinations which are found to not have nonspecific amplification signals, and "x" stands for combinations which are found to have nonspecific amplification signals, respectively.

TABLE 1

|     | L 1 | L 2 | L 3 | L 4 | L 5 | L 6 |
| --- | --- | --- | --- | --- | --- | --- |
| R 1 | ○ | ○ | ○ | ○ | ○ | ○ |
| R 2 | ○ | ○ | ○ | ○ | ○ | ○ |
| R 3 | ○ | ○ | ○ | ○ | ○ | ○ |
| R 4 | ○ | ○ | ○ | ○ | ○ | ○ |
| R 5 | X | X | X | X | X | X |
| R 6 | X | X | X | X | X | X |
| R 7 | ○ | ○ | ○ | ○ | ○ | ○ |

TABLE 2

|     | L 1 | L 2 | L 3 | L 4 | L 5 | L 6 |
| --- | --- | --- | --- | --- | --- | --- |
| R 1 | ○ | ○ | X | X | X | X |
| R 2 | ○ | ○ | X | X | X | X |
| R 3 | X | X | X | X | X | X |
| R 4 | X | X | X | X | X | X |
| R 5 | X | X | X | ○ | X | X |
| R 6 | X | X | X | X | X | X |
| R 7 | X | X | X | X | X | X |

From these results, as to the combinations of primers, only the combinations of L1/R1, L1/R2, L2/R1, and L2/R2 were promising, out of all the 42 kinds of combinations.

Example 4 Confirmation of Quantification

The confirmation of quantification was carried out with four combinations of the primer sets L1/R1, L1/R2, L2/R1, and L2/R2 that were promising according to Example 3. The confirmation of quantification was performed using SYBR (registered trademark) Premix Ex Taq II(Tli RNaseH Plus), with the following reaction composition: 12.5 µl, of SYBR (registered trademark) Premix Ex Taq II (Tli RNaseH Plus) (2×conc.), 0.5 µL of the above four combinations of each 10 µM primer mix, and 5.0 µl, of a template were mixed, and sterile water was added thereto to make up a total volume of 25 µL. The reaction mixtures that were prepared, one in which the crudely purified genome solution derived from an rAAV2 vector prepared in Example 2, one in which 10-fold serial dilutions ($1\times10^2$ copy/5 µL, $1\times10^3$ copy/5 µL, $1\times10^4$ copy/5 µL, $1\times10^5$ copy/5 µL, $1\times10^6$ copy/5 µL, or $1\times10^7$ copy/5 µL) of plasmid DNA harboring amplified region in the ITRs of AAV2 were used, and one in which sterile distilled water was used in place of the template as the negative control were used as the template. The reactions and the detection were performed according to real-time PCR, which comprised 95° C. for 2 minutes (initial denaturation), and thereafter 35 cycles of reactions, in which one cycle of reaction comprised 95° C. for 5 seconds and 60° C. for 30 seconds. In addition, after the termination of real-time PCR, the melting curve analysis was performed. Further, the calibration curve was drawn from the results of real-time PCR using plasmid DNAs of each copy number as a template, and the quantitative analysis of the crudely purified genome derived from rAAV2 vector was performed from the obtained calibration curve.

Figure 4:
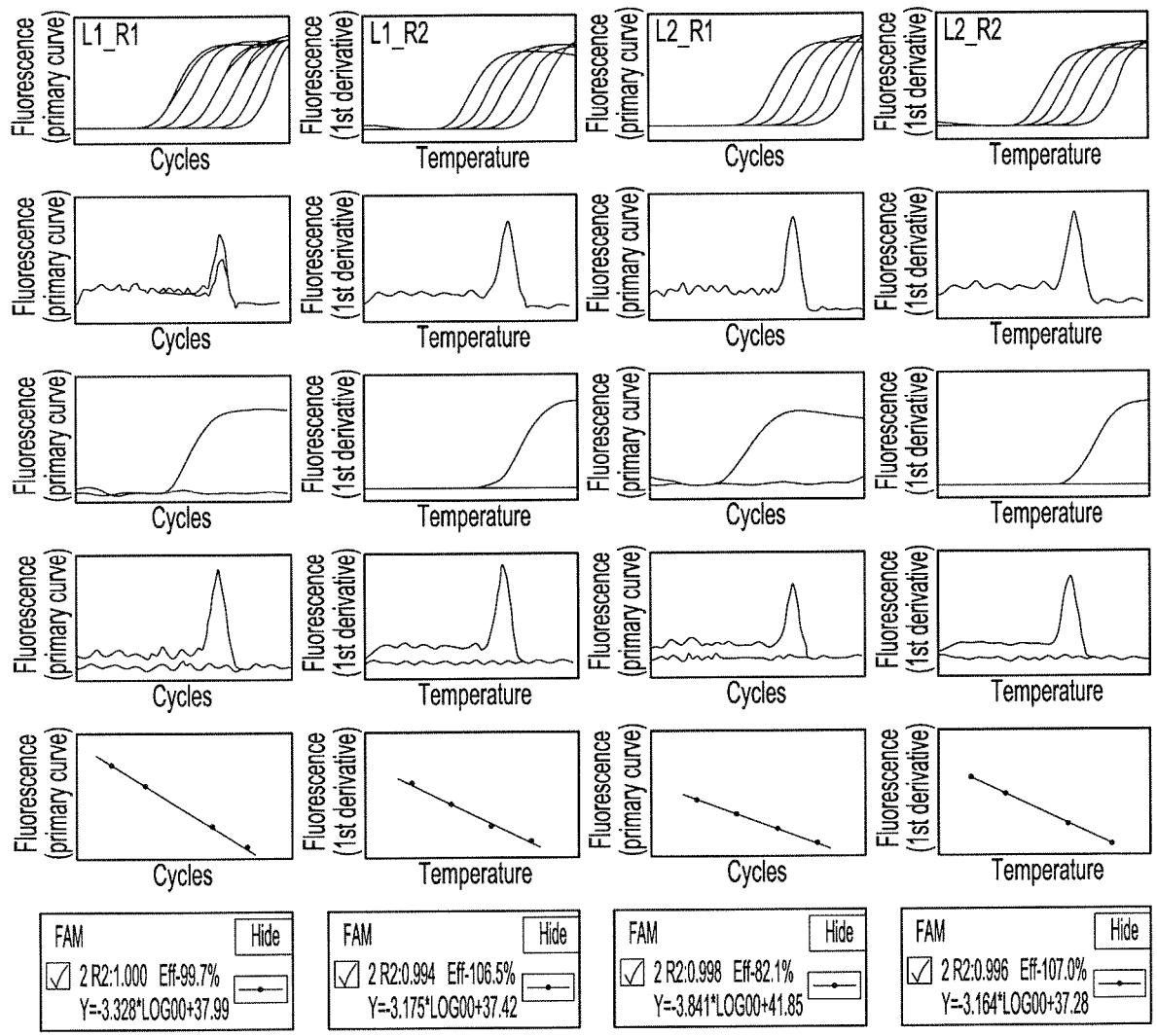
FIG. 4 Charts showing the results of real-time PCR in Example 4, wherein L1_R1 in the figure shows a reaction in which a primer L1 and a primer R1 are used as a primer pair, and as to each primer set, in the order from top to bottom, an amplification curve in a case where plasmid DNA of each copy number is used as a template, and the analytical results of melting curves in a case where plasmid DNA of each copy number is used as a template, amplification curves in a case where a crudely purified genome solution derived from rAAV2 vector is used as a template and the reaction of the negative control, the analytical results of melting curves in a case where a crudely purified genome solution derived from rAAV2 vector is used as a template and the reaction of the negative control, and a calibration curve drawn from the results of real-time PCR in which plasmid DNA of each copy number is used as a template.

The results are shown in FIG. 4. FIG. 4 shows, with respect to each of the primer sets, in the order from top to bottom, an amplification curve in a case where a plasmid DNA of each copy number is used as a template, the analytical results of melting curves in a case where a plasmid DNA of each copy number is used as a template, amplification curves in a case where a crudely purified genome solution derived from rAAV2 vector is used as a template or the reaction of the negative control, the analytical results of melting curves in a case where a crudely purified genome solution derived from rAAV2 vector is used as a template or the reaction of the negative control, and a calibration curve. As is clear from FIG. 4, all of the primer sets have excellent quantification, so that genomic DNA of rAAV2 could be quantified. Also, nonspecific amplification was not found. In the combination of L1/R1, a calibration curve of which correlation factor ($R^2$) is 1.000 was obtained within the range of from $1\times10^3$ copies to $1\times10^7$ copies of the amount of template. In addition, the reaction efficiency in a case where L1/R1 was used as the primer set within the range of this amount of template was 99.7%, which was a reaction efficiency closest to 100% among the reactions using the four kinds of primer sets. According to this example, it could be seen that the four combinations of the primer sets L1/R1, L1/R2, L2/R1, and L2/R2 were excellent as the primer sets for quantification of the genomic DNA of AAV2, among which the combination of L1/R1 was most excellent.

INDUSTRIAL APPLICABILITY

The present invention is especially useful in the fields of medicine, genetic engineering, and biology.

SEQUENCE LISTING FREE TEXT

SEQ ID NO: 1; Designed PCR primer "L1"
SEQ ID NO: 2; Designed PCR primer "L2"
SEQ ID NO: 3; Designed PCR primer "L3"
SEQ ID NO: 4; Designed PCR primer "L4"
SEQ ID NO: 5; Designed PCR primer "L5"
SEQ ID NO: 6; Designed PCR primer "L6"
SEQ ID NO: 7; Designed PCR primer "R1"
SEQ ID NO: 8; Designed PCR primer "R2"
SEQ ID NO: 9; Designed PCR primer "R3"
SEQ ID NO: 10; Designed PCR primer "R4"
SEQ ID NO: 11; Designed PCR primer "R5"
SEQ ID NO: 12; Designed PCR primer "R6"
SEQ ID NO: 13; Designed PCR primer "R7"

The invention claimed is:

1. A method for quantification of an adeno-associated virus genome, comprising the steps of:
   (a) preparing a composition comprising the following (1) to (7):
       (1) a sample;
       (2) DNA polymerase;
       (3) at least one primer pair for use in amplification of only a nucleotide sequence contained in inverted terminal repeats of an adeno-associated virus, wherein the primer pair consists of a primer consisting of a nucleotide sequence as shown in SEQ ID NO: 1 or 2 of the Sequence Listing, and a primer consisting of a nucleotide sequence as shown in SEQ ID NO: 7 or 8 of the Sequence Listing;
       (4) an intercalating dye;
       (5) reaction buffer;
       (6) divalent metal ions; and
       (7) deoxyribonucleotide triphosphates;
   (b) performing nucleic acid amplification reaction using the composition prepared in the step (a); and
   (c) detecting an amplified product obtained in the step (b).

2. The method according to claim 1, wherein the primer pair consists of a primer consisting of a nucleotide sequence as shown in SEQ ID NO: 1 of the Sequence Listing, and a primer consisting of a nucleotide sequence as shown in SEQ ID NO: 7 of the Sequence Listing.

3. The method according to claim 1, wherein the intercalating dye comprises a cyanine-based dye.

4. A titer determination method of an adeno-associated virus, including the step of quantifying an adeno-associated virus genome according to a method as defined in claim 1.

* * * * *